United States Patent
Oishi et al.

(10) Patent No.: US 7,418,855 B2
(45) Date of Patent: Sep. 2, 2008

(54) GAS SENSOR AND CONTROL METHOD THEREFOR

(75) Inventors: Hidetoshi Oishi, Utsunomiya (JP); Hirotoshi Inoue, Utsunomiya (JP); Takashi Sasaki, Shioya-gun (JP); Takashi Saito, Shioya-gun (JP)

(73) Assignee: Honda Motor Co., Ltd.

( * ) Notice: Subject to any disclaimer, the term of this patent is extended or adjusted under 35 U.S.C. 154(b) by 42 days.

(21) Appl. No.: 11/212,553

(22) Filed: Aug. 25, 2005

(65) Prior Publication Data

US 2006/0048562 A1 Mar. 9, 2006

(30) Foreign Application Priority Data

Sep. 3, 2004 (JP) ............................. P2004-257137

(51) Int. Cl.
*G01N 25/18* (2006.01)
(52) U.S. Cl. ..................................... 73/25.03; 73/25.05
(58) Field of Classification Search ................. 73/25.03, 73/25.05
See application file for complete search history.

(56) References Cited

U.S. PATENT DOCUMENTS

| | | | | |
|---|---|---|---|---|
| 1,997,659 A * | 4/1935 | Styer | ............................ | 436/138 |
| 2,591,761 A * | 4/1952 | Zaikowsky | .................. | 73/25.03 |
| 2,596,992 A * | 5/1952 | Fleming | ...................... | 73/25.03 |
| 2,965,842 A * | 12/1960 | Jacobson | .................... | 324/701 |
| 3,242,717 A * | 3/1966 | Matle et al. | .................... | 422/90 |
| 3,448,561 A * | 6/1969 | Chesterfield et al. | ............ | 95/10 |
| 3,465,503 A * | 9/1969 | Henderson | .................... | 96/113 |
| 3,763,901 A * | 10/1973 | Viland | ............................ | 141/8 |
| 4,068,021 A * | 1/1978 | Allman | ........................ | 427/116 |
| 6,277,329 B1 * | 8/2001 | Evans | ........................... | 422/80 |
| 2002/0051898 A1 * | 5/2002 | Moulthrop et al. | ............. | 429/17 |
| 2002/0092339 A1 * | 7/2002 | Lee et al. | ...................... | 73/23.2 |
| 2002/0092779 A1 * | 7/2002 | Essalik et al. | ................ | 205/781 |
| 2002/0118027 A1 * | 8/2002 | Routkevitch et al. | ......... | 324/694 |
| 2003/0022050 A1 * | 1/2003 | Barton et al. | .................. | 429/34 |
| 2004/0193379 A1 * | 9/2004 | Lillis et al. | ................... | 702/102 |
| 2004/0231509 A1 * | 11/2004 | Hartlein | ......................... | 95/18 |
| 2005/0042141 A1 * | 2/2005 | Otani et al. | .................... | 422/98 |

FOREIGN PATENT DOCUMENTS

| | | | |
|---|---|---|---|
| JP | 04348267 | * | 12/1992 |
| JP | 06-223850 | | 8/1994 |
| JP | 2003161712 | * | 6/2003 |

* cited by examiner

*Primary Examiner*—Michael Cygan
(74) *Attorney, Agent, or Firm*—Fish & Richardson P.C.

(57) ABSTRACT

A gas sensor includes a gas detection chamber into which a detection gas is introduced, a detecting element and a compensating element each disposed in the gas detection chamber, a detection device which detects the concentration of a detection target gas contained in the detection gas, in accordance with a difference in electrical resistance values between the detecting element and the compensating element, and a dehumidifying element which is provided in the gas detection chamber, and reversibly absorbs water contained in the detection gas and drains off the water absorbed in the dehumidifying element.

8 Claims, 4 Drawing Sheets

GAS SENSOR AND CONTROL METHOD THEREFOR

BACKGROUND OF THE INVENTION

Priority is claimed on Japanese Patent Application No. 2004-257137, filed Sep. 3, 2004, the contents of which are incorporated herein by reference.

FIELD OF THE INVENTION

The present invention relates to a gas sensor such as a gas-contact combustion-type hydrogen sensor, and a control method therefor.

DESCRIPTION OF RELATED ART

Conventionally, a solid high-polymer membrane-type fuel cell is provided with a cell wherein a solid high-polymer electrolytic membrane is sandwiched between a fuel electrode and an oxygen electrode, and a plurality of cells are configured in a layered stack (hereinafter referred to as a fuel cell). In the fuel cell, hydrogen is supplied to the fuel electrode as fuel, and air is supplied to the oxygen electrode as oxidant, and hydrogen ions produced at the fuel electrode due to a catalytic reaction pass through the solid high-polymer electrolytic membrane and migrate to the oxygen electrode, so that electricity is generated by an electrochemical reaction with oxygen at the oxygen electrode.

In fuel cells such as this solid high-polymer membrane-type fuel cell, conventionally, there is known in the art a protective apparatus which is provided with a hydrogen detector (gas sensor) in an exhaust system, for example, on the oxygen electrode side of the fuel cell, and if this hydrogen detector detects leakage of hydrogen from the fuel electrode through the solid high-polymer electrolytic membrane to the oxygen electrode, it shuts off the supply of fuel (for example, refer to Japanese Unexamined Patent Application, First Publication No. H06-223850).

Furthermore, as such a hydrogen detector, for example, a gas-contact combustion-type hydrogen sensor is well known. This gas-contact combustion-type hydrogen sensor is equipped with a pair of a gas detecting element which is made from a catalyst such as platinum and a temperature compensating element, and detects the concentration of hydrogen, based on, for example, a difference in electrical resistance between the gas detecting element and the temperature compensating element which is at a relatively low temperature such as an ambient temperature, when the gas detecting element reaches a relatively high temperature due to heat generated by combustion when hydrogen comes into contact with a catalyst such as platinum.

Incidentally, in the fuel cell of the solid high-polymer membrane-type fuel cell and the like as described above, in order to maintain the ion conductivity of the solid high-polymer electrolytic membrane, water (humidifying water) is mixed with the reactant gas (for example, hydrogen or air) supplied to the fuel cell, using a humidifier or the like. Moreover, since reaction-generated water is produced by the electrochemical reaction when the fuel cell is in operation, the fuel cell exhaust gas, particularly the exhaust gas from the oxygen electrode, is a high-humidity gas.

Therefore, in the protective apparatus of the fuel cell of the aforementioned conventional technology, due to highly humid off-gas discharged from the fuel cell, condensation may occur on the hydrogen detector and the like, positioned in the flow path of the off-gas. In this case, deterioration of, and damage to, the hydrogen detector may occur. In particular, in the solid high-polymer membrane-type fuel cell, since the normal operating temperature is lower than the evaporation temperature of water, and since the off-gas is highly humid and gas having high water content is discharged, there is a problem in that the moisture content of the off-gas readily condenses. Furthermore, for example, when the gas-contact combustion-type hydrogen detector is provided, particularly when provided in the exhaust system on the oxygen electrode side of the fuel cell, if electricity is supplied to the gas detecting element while humidifying water or reaction-generated water and the like is adhered to it, localized non-uniformities in temperature distribution may occur on the surface of the element, and may result in damage to, and decreased sensitivity of, the element.

SUMMARY OF THE INVENTION

The present invention was made in view of the above circumstances and the object thereof is to prevent damage to, deterioration of, and reduction in accuracy of detection of a gas sensor.

In order to achieve the above-mentioned object, the present invention provides a gas sensor including a gas detection chamber into which a detection gas is introduced, a detecting element and a compensating element each disposed in the gas detection chamber, a detection device which detects the concentration of a detection target gas contained in the detection gas, in accordance with the difference in electrical resistance values between the detecting element and the compensating element, and a dehumidifying element which is provided in the gas detection chamber, and reversibly absorbs water contained in the detection gas and drains off the water absorbed in the dehumidifying element.

According to the gas sensor, even when the relative humidity of the detection gas in the gas detection chamber is high, the relative humidity of the detection gas can be decreased by the dehumidifying element. In addition, even when condensation occurs in the gas detection chamber, any condensed water produced can be absorbed by the dehumidifying element. Accordingly, it becomes possible to prevent deterioration of the detecting element and the compensating element due to electricity supplied to the detecting element and the compensating element while the condensed water is adhered to surfaces of the detecting element and the compensating element.

The gas sensor may further include a heater which is disposed in the gas detection chamber and heats the inside of the gas detection chamber.

In this case, heat generated by the heater decreases the relative humidity inside the gas detection chamber, and the water absorbed in the dehumidifying element is drained off. As a result, the amount of absorbable water in the dehumidifying element is increased. Furthermore, even when the relative humidity is increased due to a temperature drop inside the gas detection chamber when operation of the heater is stopped, water such as moisture contained in the detection gas in the gas detection chamber can be absorbed. As a result, it becomes possible to suppress condensation in the gas detection chamber.

The dehumidifying element may include a first dehumidifying member which is disposed between an opening of the gas detection chamber, and the detecting element and the compensating element, such that the first dehumidifying member is closer to the opening than the heater is.

In this case, the first dehumidifying member can be arranged without disturbing heat conduction from the heater to the detecting element and the compensating element.

The dehumidifying element may include a second dehumidifying member disposed on an inner wall of the gas detection chamber.

The gas sensor may further include a water-repellent filter which is disposed at the inside the opening of the gas detection chamber, and permits the detection gas to pass therethrough.

The heater may have a plate shape and may be disposed such that it is located between the detecting element and the compensating element, and such that the heater follows the flow direction of the detection gas flowing into the gas detection chamber.

The gas sensor may further include a dehumidifying element temperature detecting device which detects the temperature of the dehumidifying element, a dehumidifying element temperature changing device which changes the temperature of the dehumidifying element, and a dehumidifying element temperature control device which controls the dehumidifying element temperature changing device such that the temperature of the dehumidifying element detected by the dehumidifying element temperature detecting device is set to a predetermined temperature.

In this case, the dehumidifying element can be maintained in a water-absorbable condition by setting the temperature of the dehumidifying element equal to the temperature in which water absorbed in the dehumidifying element is drained off from the dehumidifying element, and is condensed, etc., or to a predetermined temperature higher than the above-mentioned temperature. As a result, the occurrence of condensation in the gas detection chamber can be suppressed. Furthermore, the permeability of gas flowing into the gas detection chamber can be maintained.

The dehumidifying element may include a second dehumidifying member disposed on an inner wall of the gas detection chamber.

In this case, even when the inner wall of the gas detection chamber is made from metal, etc., having a relatively higher thermal conductivity and thus having a higher probability of producing condensation, the occurrence of condensation can be suppressed.

The gas sensor may further include a second detection device which, at least, detects the temperature and humidity inside the gas detection chamber.

In addition, in order to achieve the above-mentioned object, the present invention also provides a control method for a gas sensor including a gas detection chamber into which a detection gas is introduced, a detecting element and a compensating element each disposed in the gas detection chamber; a first detection device which detects the concentration of a detection target gas contained in the detection gas, in accordance with the difference in electrical resistance values between the detecting element and the compensating element, and a dehumidifying element which is provided in the gas detection chamber, and reversibly absorbs water contained in the detection gas and drains off the water absorbed in the dehumidifying element. The control method includes detecting the temperature of the dehumidifying element, and changing the temperature of the dehumidifying element to the predetermined temperature.

DETAILED DESCRIPTION OF THE INVENTION

Hereinafter, a gas sensor according to one embodiment of the present invention will be explained with reference to the figures.

Figure 1:
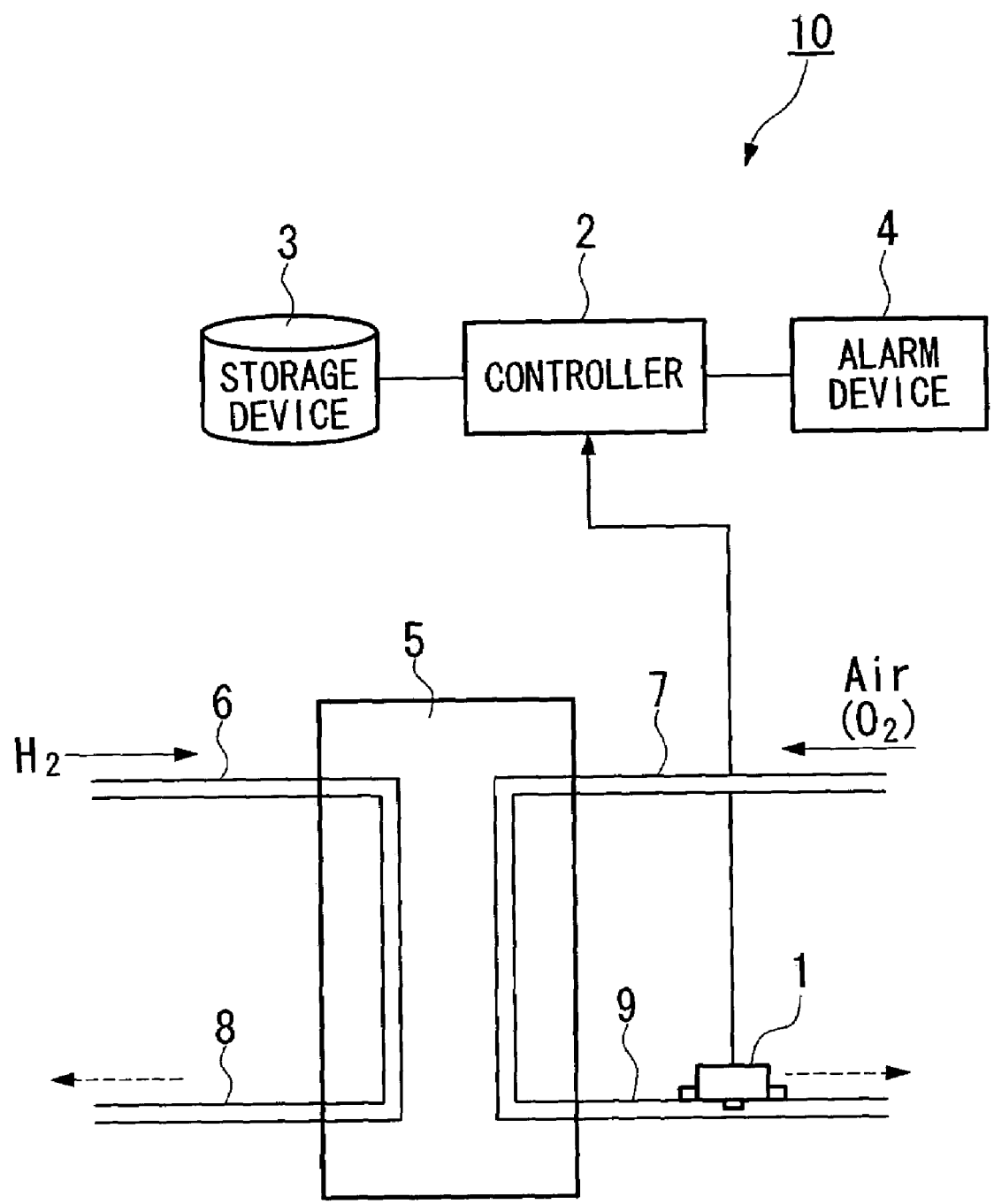
FIG. 1 is a partial configuration view of a fuel cell system having a gas sensor according to one embodiment of the present invention.

A gas sensor 1 according to the present embodiment is, for example, a hydrogen sensor for detecting hydrogen. As shown in FIG. 1, a fuel cell system 10 has a controller 2, a storage device 3, an alarm device 4, a fuel cell 5 which is a power source of a vehicle, and pipes 6, 7, 8, and 9 which are connected to the fuel cell 5 and transfer reaction gases to the fuel cell 5. In the fuel cell system 10, the gas sensor 1 is provided to the outlet side pipe 9 on an oxygen electrode side, and confirms that the hydrogen is not discharged through the outlet side pipe 9.

The controller 2 is connected to the gas sensor 1 attached to the outlet side pipe 9 on the oxygen electrode side. The controller 2 determines whether any abnormalities have occurred in the fuel cell 5 based on a comparison result of, for example, a detection signal outputted from the gas sensor 1 and a predetermined judgment-threshold stored in the storage device 3. If the controller 2 determines that the fuel cell 5 is in an abnormal condition, then the controller 2 triggers the alarm device 4 etc. The storage device 3 stores a map of the predetermined judgment-threshold with respect to the output from the gas sensor 1 corresponding to the operating conditions (for example, differential pressure between the electrodes and operating pressure, etc.) and the like.

The fuel cell 5 is mounted in the vehicle as, for example, a power source for an electric car or the like. The fuel cell 5 includes a plurality of layers of fuel cells, each fuel cell being an electrolytic electrode structure wherein a solid high-polymer electrolytic membrane is sandwiched between a hydrogen electrode and an oxygen electrode, and is further sandwiched between a pair of separators (not shown in the figures).

If a fuel gas such as hydrogen is supplied to the fuel electrode (i.e., the hydrogen electrode) through the inlet side pipe 6, the hydrogen is ionized on the fuel electrode, and migrates to the oxygen electrode through a suitably humidified solid high-polymer electrolytic membrane. In addition, electrons generated accompanying this migration are extracted to an external circuit and used as direct current electrical energy. An oxidant gas such as oxygen, or air is supplied to the oxygen electrode through the inlet side pipe 7. The hydrogen ions, the electrons, and the oxygen react on the oxygen electrode to produce water. Then, the reacted so called off-gas from both the hydrogen electrode and the oxygen electrode is discharged from the system through the outlet-side pipes 8 and 9.

Figure 2:
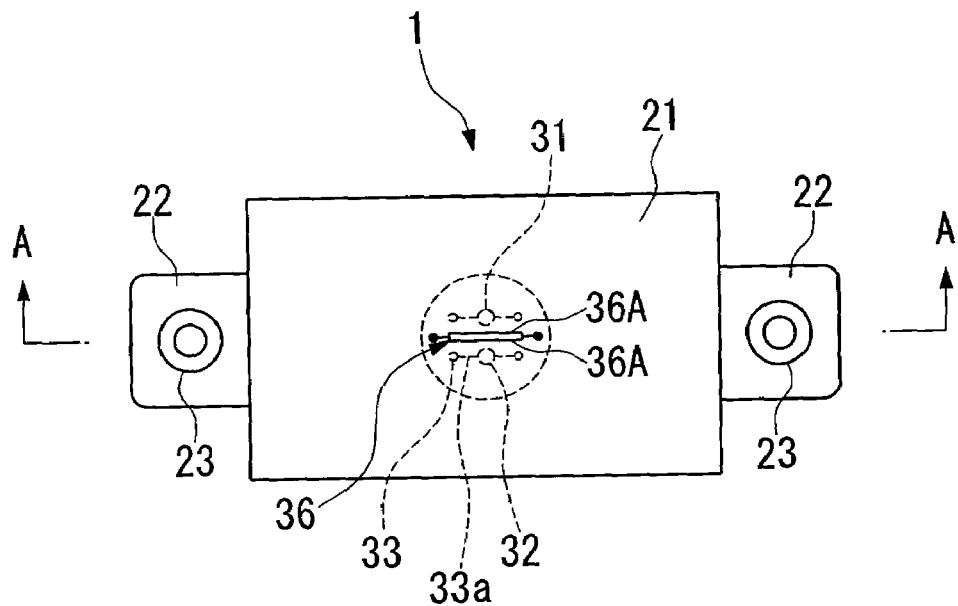
FIG. 2 is a cross-sectional view of the gas sensor shown in FIG. 1.
Figure 3:
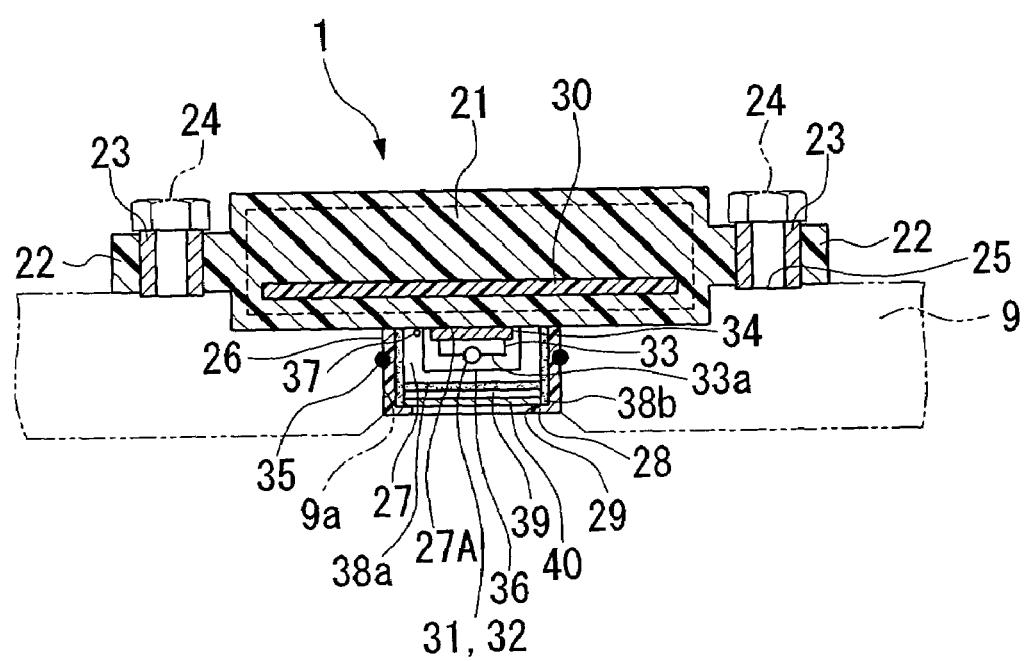
FIG. 3 is a cross-sectional view taken along the line A-A in FIG. 2.

For example, as shown in FIGS. 2 and 3, the gas sensor 1 includes a long rectangular-shaped case 21 extending along the length direction (i.e., the horizontal direction) of the outlet side pipe 9. The case 21 is made from, for example, polyphenylene sulfide, and is provided with flange parts 22 at both ends in the length direction. A collar 23 is fitted into each flange part 22, and, for example, as shown in FIG. 3, by inserting a bolt 24 into each collar 23 and tightening the bolt 24, the flange parts 22 are fixed onto mounts 25 provided on the outlet side pipe 9 on the oxygen electrode side.

For example, as shown in FIG. 3, a cylindrical part 26 is formed on one face of the case 21 in the thickness direction thereof, and the interior of the cylindrical portion 26 forms a gas detection chamber 27. A flange portion 28 is formed inwardly on an inner wall of the gas detection chamber 27, and an opening of the flange portion 28 forms a gas introduction portion 29.

In the case 21, a circuit board 30 sealed with resin is disposed, and a detecting element 31 and a temperature compensating element 32 each disposed inside the cylindrical part 26 is connected to the circuit board 30. Each of the detecting element 31 and the temperature compensation element 32 is disposed such that each is separated away from a base 34 disposed on a bottom face 27A of the gas detection chamber 27 by a predetermined distance in the thickness direction of the gas sensor 1, by means of a plurality of, for example, four stays 33 and lead wires 33a for electrical connections. Furthermore, each of the detecting element 31 and the temperature compensation element 32 is disposed such that they form a pair facing each other with a predetermined distance therebetween. A sealing member 35 is attached around the periphery of the cylindrical portion 26. The sealing member 35 provides airtightness with respect to the periphery of the cylindrical portion 26 by making airtight contact with the inner wall of a through hole 9a of the outlet side pipe 9.

The detecting element 31 is a well-known device. And as shown in, for example, FIG. 4, the detecting element 31 is constituted by covering the surface of a coil 31a of a metal line which contains platinum having a high temperature coefficient to electric resistance, etc., with a carrier such as alumina which carries a catalyst 31b consisting of noble metals, etc., which are reactive to the hydrogen (i.e., the detection target gas).

The temperature compensating element 32 is not reactive to the detection target gas, and is constituted by, for example, covering the surface of a coil 32a which is equivalent to the coil 31a of the detecting element 31, with a carrier such as alumina.

The gas sensor 1 can detect concentration of hydrogen by (i) using the difference in electrical resistance generated between the detecting element 31 which reaches a high temperature by heat generation due to the burning reaction generated when hydrogen which is the detection target gas comes into contact with the catalyst 31b of the detecting element 31, and the temperature compensation element 32 having a temperature being lower than that of the detecting element 31 because there is no generation of a burning reaction of hydrogen which is the detection target gas, and (ii) canceling the change in electrical resistance due to atmospheric temperature.

As shown in, for example, FIG. 2, an approximately rectangular-plate-shaped heater 36 is disposed in the gas detecting chamber 27 such that the heater 36 is located between the detecting element 31 and the temperature compensating element 32, and such that the heater 36 follows the flow direction of the detection gas flowing into the gas detection chamber 27. This heater 36 includes a resistor, etc., and heats the inside of the gas detecting chamber 27, the detecting element 31, and the temperature compensating element 32 by receiving electricity from the circuit board 30. The heater 36 is disposed such that heat radiation faces 36A thereof face the detecting element 31 and the temperature compensation element 32. Each surface of the heater 36 forms a heat radiation face 36A. The heater 36 equally divides the detection gas coming into the gas detection chamber 27, into one stream going to the detecting element 31 side and another stream going to the temperature compensation element 32 side.

In the gas detection chamber 27, a sensor 37 is installed for detecting temperature and humidity inside the gas detection chamber 27.

Figure 4:
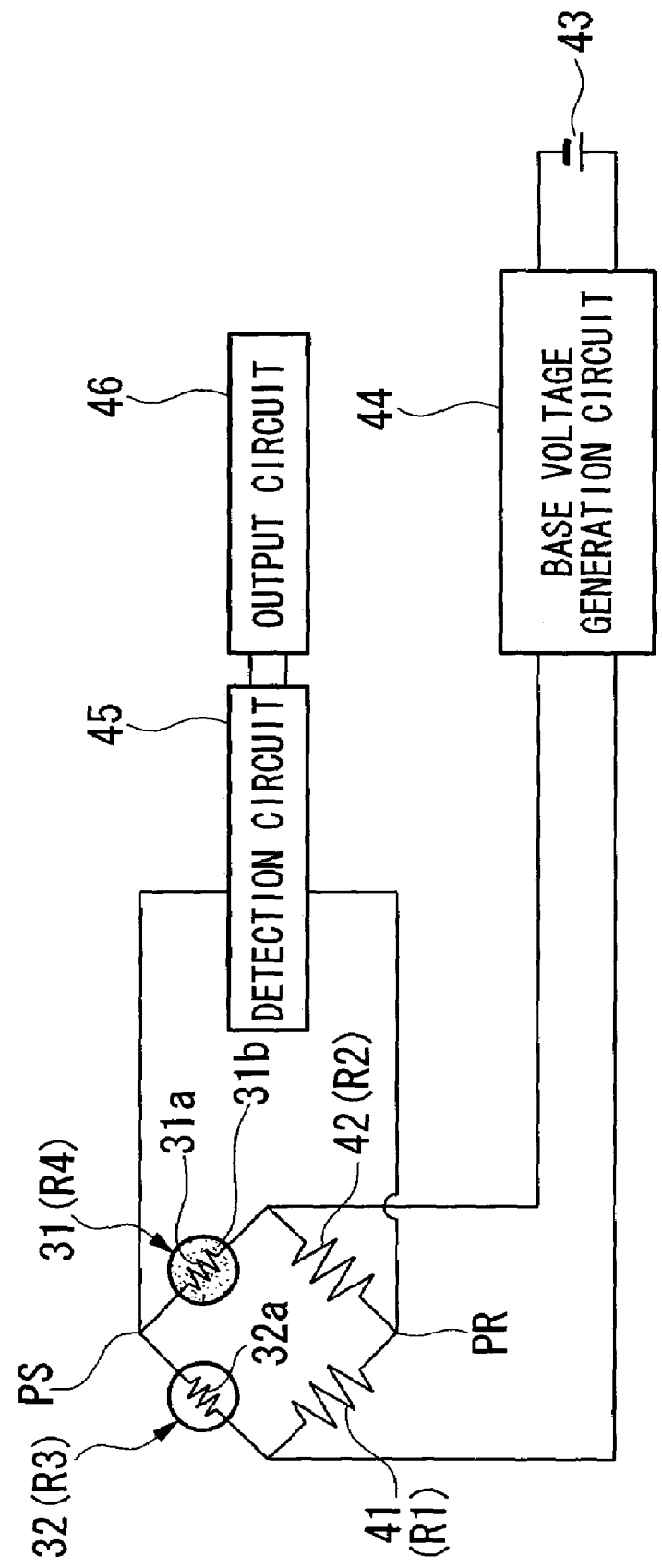
FIG. 4 is a circuit diagram of the gas sensor shown in FIG. 1.

As shown in FIG. 4, the gas sensor 1 is equipped with a bridge circuit in which a branch constituted by connecting the detecting element 31 (resistance R4) and the temperature compensating element 32 (resistance R3) in series and a branch constituted by connecting a fixed resistance 41 (resistance R1) and a fixed resistance 42 (resistance R2) in series, are connected in parallel to a base voltage generation circuit 44 which supplies the predetermined base voltage based on voltage supplied from an external power supply 43. In the bridge circuit, a detection circuit 45 is connected to a connecting point PS between the detecting element 31 and the temperature compensating element 32, and a connecting point PR between the fixed resistances 41 and 42, in order to detect voltage between the connecting points PS and PR. Furthermore, an output circuit 46 is connected to the detection circuit 45.

When hydrogen which is the detection target gas does not exist in the detection gas introduced into the gas detecting chamber 27, the bridge circuit balances, and is in the state of R1×R4=R2×R3, and the output of the bridge circuit becomes zero. On the other hand, if hydrogen exists, since hydrogen will burn at the catalyst 31b of the detecting element 31 to increase temperature, the resistance R4 will be increased. On the other hand, hydrogen will not be burned at the temperature compensating element 32, and therefore the resistance R3 will not be changed. As a result, the balance of the bridge circuit breaks, and the voltage which has a tendency to increase according to an increase in the hydrogen concentration is applied to the detection circuit 45. The detected value of voltage outputted from the detection circuit 45 is transferred to the output circuit 46, and the output circuit 46 outputs the detected value inputted therein to the controller 2. In the controller 2, the hydrogen concentration is calculated based on change in the detected value of voltage, referring to the map of the hydrogen concentration which is set up beforehand, etc.

In the gas detection chamber 27, a dehumidifying element 38a is disposed at a position between the gas introduction portion 29, and the elements 31 and 32, and is shifted closer to the gas introduction portion 29 side than the heater 36 is. Furthermore, a dehumidifying element 38b is disposed such that an inner wall surface of the cylindrical portion 26 is covered with the dehumidifying element 38b.

Each of the dehumidifying elements 38a and 38b is made from an absorption material which absorbs water corresponding to the humidity conditions in a gas therearound, such as, for example, silica gel, zeolite, activated carbon, activated alumina, and water-absorption polymer. Water absorbed in the dehumidifying elements 38a and 38b can be discharged therefrom and can be evaporated into the gas therearound by heating the dehumidifying elements 38a and 38b using the heater 36, or the like. Each of the dehumidifying elements 38a and 38b is an absorption material which reversibly absorbs water therearound and drains off water therein.

At a position shifted closer to the gas introduction portion 29 side than the dehumidifying element 38a, there are provided, in series towards the gas introduction portion 29, a sintered filter 39 and a water-repellent filter 40, each of which permits the detection gas to pass therethrough.

That is, off-gas passing inside the outlet side pipe 9 passes through, in series, the water-repellent filter 40 and the sintered filter 39, and then flows into the gas detection chamber 27.

The controller 2 is connected to the sensor 37 and the heater 36 in the gas detection chamber 27. The controller 2 controls operating conditions (for example, timing of starting and stopping the supply of electricity, and the amount of electricity supplied, and etc.) of the detecting element 31, the temperature compensating element 32, and the heater 36, in accordance with temperature and humidity in the atmospheric gas in the gas detection chamber 27, which are outputted from the sensor 37 or the like, or in accordance with load conditions and operating conditions of the fuel cell 5, etc.

The controller 2 controls the amount of electricity supplied to the heater 36 by, for example, feedback control of the current value supplied to the heater 36, or by chopper control based on, for example, on/off operation of a switching element (that is, on/off switching control of the electricity supplied to the heater 36) or the like. The controller 2 maintains the temperature inside the gas detection chamber 27 detected by the sensor 37 within a predetermined temperature range which is, at least, higher than a dew point temperature, by controlling electricity supplied to the heater 36 in accordance with the temperature detected by the sensor 37. In addition, the controller 2 controls timing of starting and stopping electricity and the amount of electricity supplied to the heater 36, such that the relative humidity inside the gas detection chamber 27 which is detected by the sensor 37 is set to, for example, the relative humidity within a predetermined humidity range, or to the relative humidity searched in a map which is prepared in advance and shows the relative humidity corresponding to the temperature inside the gas detection chamber 27, etc.

Furthermore, in addition to the temperature conditions inside the gas detection chamber 27 which is detected by the sensor 37, the controller 2 controls the amount of electricity supplied to the heater 36 in accordance with (i) operating conditions of the: fuel cell 5 (i.e., operating conditions including starting operation and stopping operation of the fuel cell 5), (ii) load conditions of the fuel cell 5 in operation, (iii) an electricity generating instruction for the fuel cell 5 (i.e., FC output instruction value), (iv) the output current value from the fuel cell 5 which is detected by an output current sensor (not shown in figures), and (v) power generating states of the fuel cell 5 which are calculated based on a detected flow rate of air supplied from an air compressor (not shown in the figures) to the fuel cell 5 which is detected by a flow rate sensor (not shown in the figures) or the like.

When the load condition of the fuel cell 5 is changed to a high-load condition or the like, if there are possibilities of (a) decreasing the temperature inside the gas detection chamber 27 of the gas sensor 1 which is exposed to the off-gas, due to the increase in the flow rate of the off-gas passing inside the outlet side pipe 9 on the oxygen electrode side, or (b) increasing the relative humidity inside the gas detection chamber 27 due to the increase in the amount of produced water contained in the off-gas produced at the fuel cell 5, then the controller 2 increases the temperature inside the gas detection chamber 27 by increasing the supply current to the heater 36. By doing this, condensation in the gas detection chamber 27 can be prevented. On the other hand, when the load condition of the fuel cell 5 is changed to a low-load condition or the like, the controller 2 suppresses excessive energy consumption by decreasing the supply current to the heater 36.

When the fuel cell 5 is in the stopped condition or the like, if a purging process for discharging water remaining in the fuel cell system to the outside by increasing the flow rate of the off-gas passing through each of the outlet side pipes 8 and 9 is executed, then the controller 2 temporarily increases the temperature inside the gas detection chamber 27 by increasing the current supplied to the heater 36. By doing this, the saturated vapor amount in the atmospheric gas inside the gas detection chamber 27 is increased, thereby preventing condensation in the gas detection chamber 27.

When starting the operation of the fuel cell 5, the controller 2 starts supplying electricity to each of the detecting element 31 and the temperature compensating element 32 of the gas sensor 1 and to the heater 36, before starting the flow of the off-gas inside the outlet side pipe 9 on the oxygen electrode side. Furthermore, when stopping the operation of the fuel cell 5, the controller 2 stops supplying electricity to each of the elements 31 and 32 of the gas sensor 1 and to the heater 36, after stopping the flow of the off-gas inside the outlet side pipe 9 on the oxygen electrode side.

Next, an operation of the gas sensor 1 of the present embodiment will be explained below.

Each of the dehumidifying elements 38a and 38b disposed in the gas detection chamber 27 absorbs or drains off water, based on the humidity conditions in the atmospheric gas.

For example, when the electricity is supplied to the heater 36 while the gas sensor 1 is in operation, since the temperature in the gas detection chamber 27 rises relatively, the relative humidity in the gas detection chamber 27 decreases, and each of the dehumidifying elements 38a and 38b is maintained in the dried condition (that is, maintained in the condition in which the absorbable amount of water is increased).

Accompanying stopping of the operation of the fuel cell 5, the supply of electricity-to the heater 36 is stopped after stopping the off-gas flowing inside the outlet side pipe 9 on the oxidant electrode side, thereby increasing the relative humidity inside the gas detection chamber 27 accompanied by the temperature drop inside the gas detection chamber 27. At this time, each of the dehumidifying elements 38a and 38b absorbs water including vapor contained in the atmospheric gas in the gas detection chamber 27, corresponding to the absorbable water amount thereof. By this, it becomes possible to prevent condensation in the gas detection chamber 27, that is, it becomes possible to prevent the relative humidity in the gas detection chamber 27 reaching 100%, or the temperature in the gas detection chamber 27 dropping to equal to or lower than the dew point temperature. In addition, even when condensation occurs due to the temperature drop partially occurring in the gas detection chamber 27 below the dew point temperature, the condensed water can be absorbed by the dehumidifying elements 38a and 38.

In particular, the dehumidifying element 38a disposed between the gas introduction portion 29, and the detecting element 31 and the temperature compensating element 32, and shifted closer to the gas introduction portion 29 side than the heater 36 can decrease the relative humidity of the atmospheric gas in which the detecting element 31 and the temperature compensating element 32 are exposed, thereby preventing the occurrence of condensation on the surfaces of the elements 31 and 32.

In addition, by forming the dehumidifying element 38b which covers the inner surface of the cylindrical portion 26 using materials such as metals which have relatively higher thermal conductivity than that inside the gas detection chamber 27, condensation which easily occurs on the inner wall surface can be suppressed.

As explained above, according to the gas sensor 1 of the present embodiment, water contained in steam in the atmospheric gas inside the gas detection chamber 27 can be absorbed by the dehumidifying elements 38a and 38b, even when the surface temperatures of the detecting element 31 and the temperature compensating element 32 drop due to stopping an operation of the heater 36, which can change the temperature conditions and the humidity conditions of the atmospheric gas inside the gas detection chamber 27, and which can further change the temperature conditions of the surfaces of the detecting element 31 and the temperature compensating element 32. As a result, occurrence of the condensation inside the gas detection chamber 27 can be suppressed since the relative humidity in the atmospheric gas inside the gas detection chamber 27 is decreased, and since it is possible to suppress the temperature of the atmospheric gas inside the gas detection chamber 27 or temperatures of the surfaces of the detecting element 31 and the temperature compensating element 32 from being equal to or lower than a dew point temperature.

In addition, even when condensation occur accompanied by a local temperature drop or the like due to stoppage of the operation of the heater 36, the produced condensation can be absorbed by the dehumidifying elements 38a and 38b. As a result, it is possible to prevent condensation occurring at the gas sensor 1 when an operation of the gas sensor 1 starts. Furthermore, it is also possible to lower, in advance, the relative humidity inside the gas detection chamber 27 in order to prepare for the next starting of the operation thereof.

Moreover, in the present embodiment, the hydrogen sensor is used for the gas sensor 1; however, the gas sensor 1 is not limited to the hydrogen sensor, and other gas sensors may be used which detect, for example, inflammable gases such as carbon monoxide or methane.

In addition, in the present embodiment, the gas-contact combustion-type sensor is used for the gas sensor 1; however, the gas sensor 1 is not limited to the gas-contact combustion-type sensor, and other types of sensors may be used such as a semiconductor type sensor.

In addition, in the present embodiment, the bridge circuit is used for the circuit including the detecting element 31 and the temperature compensating element 32 connected to each other; however, the circuit is not limited to the bridge circuit, and other types of circuits such as a series circuit may be adopted. In this case, as other parameters corresponding to the resistance R4 of the detecting element 31, voltages or currents between predetermined points may be outputted to the controller 2.

In addition, in the present embodiment, the heater 36 is disposed between the detecting element 31 and the temperature compensating element 32; however, the location of the heater 36 is not limited to this, and the heater 36 may be disposed at, for example, any locations between the gas introduction portion 29, and the detecting element 31 and the temperature compensating element 32 inside the gas detection chamber 27, that are shifted closer to the detecting element 31 and the temperature compensating element 32 side than the location of the dehumidifying element 38a.

A variant example of the present embodiment will be explained below.

Moreover, in the following explanation, explanations for the same components as in the above-mentioned embodiment will be omitted.

Figure 5:
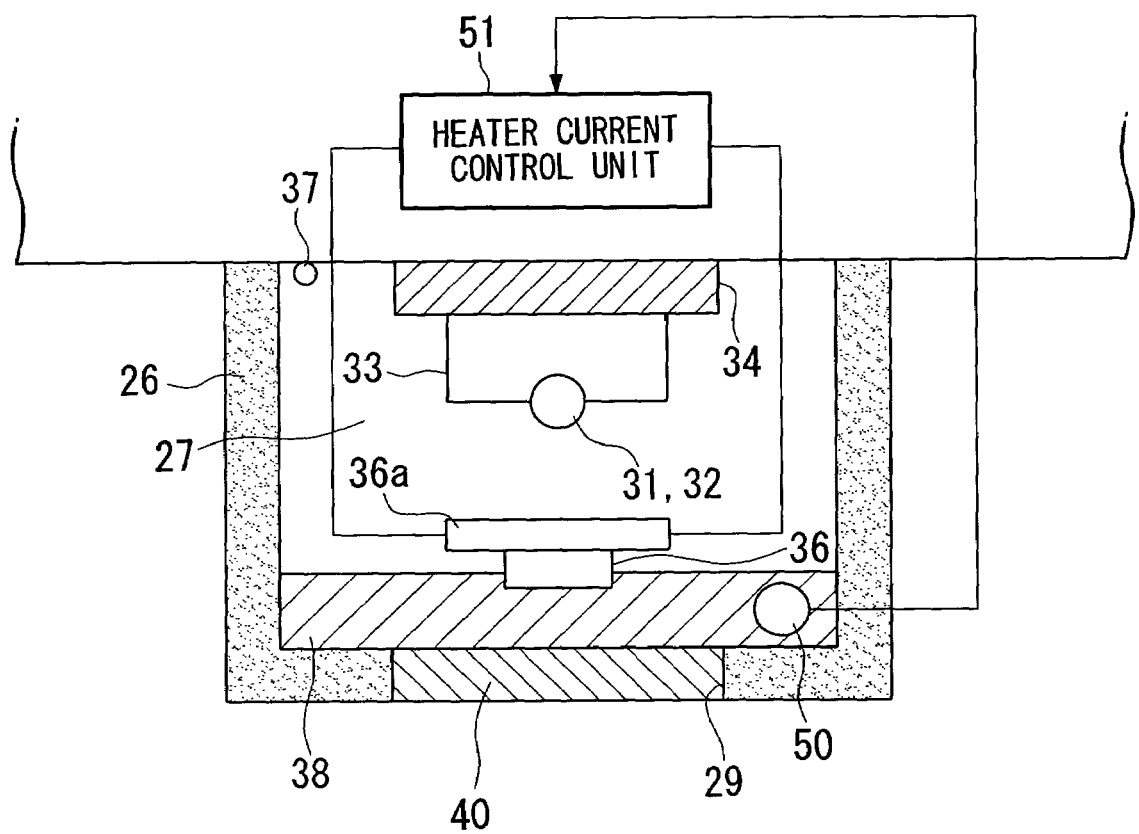
FIG. 5 is a cross-sectional view of a gas sensor according to a modified example of the embodiment.

In the variant example, as shown in FIG. 5, a water-repellent filter 40 is disposed inside the gas introduction portion 29, and a dehumidifying element 38 made from an absorption material which absorbs water corresponding to the humidity conditions in the atmospheric gas, such as, for example, silica gel, zeolite, activated carbon, activated alumina, and water-absorption polymer is disposed in the gas detection chamber 27 adjoining the water-repellent filter 40.

The dehumidifying element 38 is equipped with a dehumidifying element temperature sensor 50. A detected temperature signal of the dehumidifying element 38 detected by the dehumidifying element temperature sensor 50 is outputted to a heater current control unit 51 provided in the controller 2.

A heater 36 made from a suitable resistor, of which the supply of current thereto is controlled by the heater current control unit 51, directly contacts the dehumidifying element 38 such that the heater 36 and dehumidifying element 38 form one component. The heater current control unit 51 controls the electrical power supplied to the heater 36 such that the temperature of the dehumidifying element 38 detected by the dehumidifying element temperature sensor 50 becomes (i) a predetermined temperature such as the temperature in which water absorbed in the dehumidifying element 38 is vaporized and is discharged from the dehumidifying element 38, or (ii) a suitable temperature higher than the predetermined temperature.

By adopting the above-mentioned configuration, the dehumidifying element 38 can be maintained in a water-absorbable condition, and condensation in the gas detection chamber 27 can be suppressed. Furthermore, permeability of the detection gas to be introduced into the gas detection chamber 27 when the detection gas passes through the dehumidifying element 38 can be secured.

Furthermore, in this variant example, a plurality of dehumidifying elements 38 may be disposed on the inner wall surface of the gas detection chamber 27.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A gas sensor comprising:
    a gas detection chamber into which a detection gas is introduced;
    a detecting element and a compensating element each disposed in the gas detection chamber and exposed to the detection gas;
    a first detection device which detects concentration of a detection target gas contained in the detection gas as a function of the difference in electrical resistance values between the detecting element and the compensating element;
    a dehumidifying element which is provided in the gas detection chamber, and reversibly absorbs water contained in the detection gas and drains off the water absorbed in the dehumidifying element; and
    a heater which changes the temperature of the dehumidifying element, wherein heating the dehumidifying element drains off the water absorbed in the dehumidifying element;
    wherein the dehumidifying element and the heater together prevent condensation within the gas detection chamber, and
    wherein the dehumidifying element includes a second dehumidifying member disposed on an inner wall of the gas detection chamber.

2. The gas sensor according to claim 1, wherein the heater is disposed in the gas detection chamber and heats inside the gas detection chamber.

3. The gas sensor according to claim 2, wherein
the dehumidifying element includes a first dehumidifying member which is disposed between an opening of the gas detection chamber, and the detecting element and the compensating element, such that the first dehumidifying member is closer to the opening than the heater.

4. The gas sensor according to claim 3, further comprising a water-repellent filter which is disposed inside the opening of the gas detection chamber, and permits the detection gas to pass therethrough.

5. The gas sensor according to claim 2, wherein
the heater has a plate shape and is disposed such that the heater is located between the detecting element and the compensating element, and such that the heater follows the flow direction of the detection gas flowing into the gas detection chamber and extends past the detecting element and compensating element in a direction toward an entry of the gas detection chamber.

6. The gas sensor according to claim 1, further comprising:
a dehumidifying element temperature detecting device which detects temperature of the dehumidifying element; and
a dehumidifying element temperature control device which controls the heater such that the temperature of the dehumidifying element detected by the dehumidifying element temperature detecting device is set to a predetermined temperature.

7. The gas sensor according to claim 1, further comprising:
a second detection device which, at least, detects temperature and humidity inside the gas detection chamber.

8. A gas sensor comprising:
a gas detection chamber into which a detection gas is introduced;
a detecting element and a compensating element each disposed in the gas detection chamber and exposed to the detection gas;
a first detection device which detects concentration of a detection target gas contained in the detection gas as a function of the difference in electrical resistance values between the detecting element and the compensating element;
a dehumidifying element which is provided in the gas detection chamber, and reversibly absorbs water contained in the detection gas and drains off the water absorbed in the dehumidifying element; and
a heater which changes the temperature of the dehumidifying element, wherein heating the dehumidifying element drains off the water absorbed in the dehumidifying element,
wherein the dehumidifying element and the heater together prevent condensation within the gas detection chamber, and
wherein the heater has a plate shape and is disposed such that the heater is located between the detecting element and the compensating element, and such that the heater follows the flow direction of the detection gas flowing into the gas detection chamber and extends past the detecting element and compensating element in a direction toward an entry of the gas detection chamber.

* * * * *